(12) United States Patent
Kumar et al.

(10) Patent No.: US 7,365,204 B2
(45) Date of Patent: Apr. 29, 2008

(54) PROCESS FOR THE PRODUCTION OF PYRIDINE AND PICOLINES

(75) Inventors: Rajiv Kumar, Pune (IN); Praphulla Narahar Joshi, Pune (IN); Gopal Moreshwar Chaphekar, Pune (IN); Prashant Suresh Niphadkar, Pune (IN); Ashutosh Agarwal, Noida (IN); Pradeep Kumar Verma, Noida (IN); Kumar Samir Singh, Noida (IN)

(73) Assignees: Council of Scientific and Industrial Research, New Delhi (IN); Jubliant Organosys Limited, Uttar Pradesh (IN)

( * ) Notice: Subject to any disclaimer, the term of this patent is extended or adjusted under 35 U.S.C. 154(b) by 354 days.

(21) Appl. No.: 10/806,061

(22) Filed: Mar. 22, 2004

(65) Prior Publication Data

US 2005/0209457 A1  Sep. 22, 2005

(51) Int. Cl.
*C07D 213/08* (2006.01)
*C07D 213/12* (2006.01)

(52) U.S. Cl. ..................... 546/253; 546/251
(58) Field of Classification Search ............. 546/153, 546/253, 251
See application file for complete search history.

(56) References Cited

U.S. PATENT DOCUMENTS 5,218,122 A * 6/1993 Goe et al. ............. 546/251
6,281,362 B1 * 8/2001 Iwamoto et al. ....... 546/345

FOREIGN PATENT DOCUMENTS

JP   2000191642   7/2000
WO  2005/000816  * 1/2005

OTHER PUBLICATIONS

Patent Abstracts of Japan of JP 2000 191642 dated Jul. 11, 2000.

* cited by examiner

*Primary Examiner*—D. Margaret Seaman
(74) *Attorney, Agent, or Firm*—Ladas and Parry LLP

(57) ABSTRACT

An process for the preparation of pyridine and/or picolines is disclosed. The process comprises contacting a mixture of carbonyl compound with ammonia in the presence of surface-passivated titanium-silicate catalyst in gas phase at a temperature ranging between 300-500° C., at gas space velocity in the range of 300 to 3000 $h^{-1}$ and at a pressure ranging between 1 to 10 atmosphere, condensing and separating the products by conventional methods and if desired, further purifying the product using well known conventional methods.

20 Claims, No Drawings

PROCESS FOR THE PRODUCTION OF PYRIDINE AND PICOLINES

FIELD OF THE INVENTION

The present invention relates an improved catalytic process for the production of pyridine and picolines. More particularly the present invention relates to a catalytic process for the production of pyridine and picolines in a single step by contacting a carbonyl compound such as an aldehyde represented by formaldehyde, acetaldehyde, propionaldehyde and/or a ketone such as acetone, propionone and the like with ammonia over a bed of porous solid catalyst(s) in gas phase aiming at increased high activity, selectivity and over all productivity.

BACKGROUND OF THE INVENTION

Pyridine and picolines (where a methyl group, attached to the carbon ring, can be present at three different regio positions, with respect to ring nitrogen, such as 2-methyl pyridine or α-picoline, 3-methyl pyridine or β-picoline and 4-methyl pyridine or γ-picoline) are important intermediate compounds in the manufacture of agricultural chemicals (like herbicides and pesticides) and pharmaceuticals. They are also useful as specific solvent in different industries like textile, polymer & pharmaceuticals.

Although, the pyridine and picolines can be obtained as by-products in coal tar industry, the preferred method for obtaining pyridine and picolines is by chemical synthesis, mainly because of small amount of pyridine and picolines present in coal tar. Chemical method for the synthesis of these pyridines and picolines is based on a catalytic process where carbonyl compounds such as an aldehyde represented by formaldehyde, acetaldehyde, propionaldehyde and/or a ketone such as acetone, propionone and the like are reacted with ammonia in gas phase over a bed of solid catalyst such as amorphous silica-alumina (see for example U.S. Pat. No. 2,807,618) and crystalline aluminosilicates, which are commonly known as zeolites (see for example U.S. Pat. No. 5,994,550).

Alumino-silicate zeolites and their metallosilicate analogues are crystalline, microporous silica based materials having different framework structures. When a trivalent metal ion like $B^{3+}$, $Al^{3+}$, $Fe^{3+}$, $Ga^{3+}$, $As^{3+}$ etc. are incorporated in a crystalline silica network, a net negative charge is generated on the framework. This net negative charge is balanced by another extra framework charge compensating, ion-exchangeable cation. When proton is present as charge compensating cation then there is no net negative charge generated and the zeolite framework remains neutral without ion-exchange property. Although, such zeolite having certain tetrahedral metal ions, particularly transition metal ions other than Si, with neutral framework do not exhibit proton donating Bronsted acidity, it is likely depending upon the chemical nature of the incorporated metal ion other than Si that these zeolites exhibit remarkable redox (see for example Kumar et al., SYNLETT, Year 1995 pages 289-298) and Lewis acid characteristics (see for example M. Shashidharan and R. Kumar, 'Titanium-silicate molecular sieves (TS-1 & TS-2) catalyzed Michael reaction of silylenolethers with α,β unsaturated carbonyl compounds', Catalysis Letters, volume 38, year 1996, pages 251-254, and M. Shashidharan et al. 'Titanium-silicate molecular sieve, TS-1, catalyzed C—C bond formation in Mukaiyama type aldol reactions' Chemical Communications, year 1996, pages 129-130).

Aiming to improve the overall yield of desired pyridine and picolines, various zeolite catalysts where frame work aluminum is replaced either fully or partially, by one or more cation(s) selected from divalent cations like $Co^{2+}$ (see U.S. Pat. No. 6,281,362) trivalent metal ions like $Fe^{3+}$ and/or $Ga^{3+}$ (see U.S. Pat. No. 4,810,794) or tetravalent metal ions like $Ti^{4+}$ (see U.S. Pat. No. 6,281,362), in the zeolite tetrahedral framework, commonly known as metallo-silicate analogues of their corresponding alumino-silicate zeolites, are also used as catalyst. For example, in U.S. Pat. No. 4,810,794 Shimizu et al and in U.S. Pat. No. 5,952,258 Saitoh et al have claimed the use of a zeolite having Si and B, Al, Fe, and/or Ga as zeolite constituent element, where an atomic ratio of Si to B, Al, Fe and/or Ga of 12 to 1000, as catalyst for producing pyridine and picolines. Among a large number of zeolites with different structure or topology used as catalyst, zeolite with MFI type topology, commonly known as ZSM-5, provides superior performance.

However, the main drawback of these catalysts was relatively low yields of desired pyridine or picolines and quick deactivation of the catalyst. In order to improve the yield of the main products (pyridine or picolines) and catalysts life, other metal ions selected from group I to XVII are deposited on the zeolite catalyst via post synthesis modification (see for example U.S. Pat. Nos. 4,810,794; 4,866,179, 5,994,550 and 6,281,362). Recently, in U.S. Pat. No. 6,281,362 Iwamoto teaches that when a catalyst comprising Ti and/or Co along with Silica as zeolite constituent, commonly known as titanium-silicate and/or cobalt silicate having MFI or MEL (commonly known as pentasil structure) zeolite framework and preferably loaded with Pb, Tl etc., is contacted with an aldehyde or ketone and ammonia in gas phase in the temperature range of 300-700° C., the overall yield of picolines is improved substantially compared to when Al, Fe and/or Ga was used as zeolite constituent along with Silica. From above mentioned prior art methods for the production of pyridine and picolines, it can be construed that not only zeolite structure, a physical factor, but also the different metal constituent present both in the zeolite framework (as zeolite constituent) and non-framework positions (loaded by conventional post synthesis treatment), known as chemical factors, significantly influence the activity, selectivity and overall productivity of the catalyst.

However, in the above mentioned prior art method for producing pyridines and picolines using solid zeolite catalyst particularly titanium-silicate catalyst do not provide the effect of the passivation of the external surface of the catalyst and the crystal size. These are very important factors, which can affect significantly both the catalytic activity and the selectivity towards desired products, because in addition to the chemical characteristics of zeolites like the chemical nature of metal ions present in the zeolite structure, physical or morphological nature of the crystals can also significantly influence the activity, selectivity and productivity of a zeolite catalyst in a given reaction. For example, shape and size of the zeolite crystals, hereinafter denoted as crystallites, having same ZSM-5 frame work structure and same chemical constituents significantly influence the activity, selectivity and productivity in shape selective reactions like xylene isomerization (see for example: Influence of crystal size of ZSM-5 on activity and selectivity in xylene isomerization by Ratnasamy et al in journal Zeolites volume 5, pages 98-100 published in March 1986). In general, smaller crystallites are more active and less shape selective. However, there exists an optimum value of the crystallite size to achieve the maximum possible productivity of the catalyst in a given catalytic application.

Further, the non-selective contribution of external surface of the crystallites also depends on the morphology of the crystallites. The selective passivation of the external surface of the crystallites by conventional post-synthesis methods like treating the zeolite crystallites with silicon tetrachloride or silicon tetraethoxide (see for example W. W. Kaeding and S. A. Butter, U.S. Pat. No. 3,911,041 in 1975 and M. Niwa et al. in Journal of Chemical Society Faraday—I, volume 81, page 2757 and year 1985) may also lead to improved selectivity of the desired products.

OBJECTS OF THE INVENTION

It is an important object of the present invention to provide an improved catalytic process for the production of pyridine and picolines for high through-put production of pyridine and picolines in gas phase.

Another objective of the present invention is to provide intrinsically highly active, selective, productive and stable catalyst for the production of pyridine and picolines in gas phase in the temperature at about 300 to 600° C.

It is still another object of the present invention to provide process that can produce pyridine and picolines in higher yields using a catalyst with higher activity and productivity than what is known in the prior-art.

SUMMARY OF THE INVENTION

The above and other objects of the present invention are achieved by the process of the present invention which comprises contacting a mixture of carbonyl compound with ammonia in the presence of surface-passivated titanium-silicate catalyst in gas phase at a temperature ranging between 300-500° C., at gas space velocity in the range of 300 to 3000 $h^{-1}$ and at a pressure ranging between 1 to 10 atmosphere, condensing and separating the products by conventional methods, optionally further purified using well known conventional methods to obtain the products.

Preferably, the carbonyl compound may be an aldehyde represented by formaldehyde, acetaldehyde, propionaldehyde or a ketone such as acetone, propionone and the like.

The catalyst used may have the molecular formula 1 $SiO_2$:x $TiO_2$, where x may be in the range of 0.005 and 0.05, having well crystalline characteristic structure characterized by powder X-ray diffraction pattern as described in Table 1.

The crystallite size of the catalyst used is in the range of 0.1-1.5 micron, and more preferably in the range of 0.3-0.8 micron.

Preferably, the crystallites of titanium silicate catalysts are treated with silicon tetrachloride or silicon tetraalkoxide using chemical vapour deposition method.

The silicon tetraalkoxides may preferably, be selected from silicon-tetra-methoxide, silicon-tetra-ethoxide silicon-tetra-isopropoxide silicon-tetra-butoxide and the like.

Preferably, the titanium-silicate catalyst is then loaded with other metal like lead, nickel, thallium or mixtures thereof.

The solid powder catalyst can optionally be mixed with inert binding substances like silica, alumina or mixture thereof and shaped in to extrudates or pallets as desired, dried and calcined or spray dried to obtain desired particle size, preferably in the range of 50-100 microns.

DETAILED DESCRIPTION

The present invention is based on the finding that when the external surface of the titanium-silicate with MFI or MEL framework structure is selectively passivated either directly by in situ deposition of silica during the process of the preparation of the catalyst after suitably modifying the method described in U.S. Pat. No. 5,885,546 and Indian Patent Application 702/DEL/94 or by appropriate conventional post synthesis modifications, the activity, selectivity and above all, the productivity of the catalyst is improved significantly. Further, it was also found that a certain range of the crystallite size of Ti-silicate catalyst also enhances the productivity of the catalyst in terms of pyridine and picolines yields per kg of the catalyst per hour.

Accordingly, the present invention provides an improved catalyst with very high intrinsic catalytic activity and efficiency for producing pyridine and picolines. This is achieved by reacting in a gas-phase an aliphatic aldehyde, aliphatic ketone or mixture thereof with ammonia in the presence of a zeolite containing titanium and silicon as zeolite constituent elements in which the atomic ratio of silicon to titanium is about 10 to about 500, prepared by suitably modifying the method described in U.S. Pat. No. 5,885,546 and Indian Patent Application 702/DEL/94 so that titanium-silicate zeolites with different crystallite sizes can be obtained.

Another feature of the present invention is that the titanium-silicate zeolite is prepared in such a way that the external surface of the titanium-silicate zeolite crystallites is passivated by selective in-situ deposition of silica on to the external surface of the crystallites.

Yet another feature of the present invention is that the selective passivation of the external surface of the titanium-silicate zeolite crystallites is carried out using conventional post-synthesis methods like treating the zeolite crystallites with silicon tetrachloride or silicon tetraethoxide.

Another feature of the present invention is that the aliphatic aldehyde is preferably an aliphatic aldehyde or ketone having 1 to 5 carbon atoms. Examples thereof include aliphatic aldehydes such as formaldehyde, acetaldehyde, propionaldehyde, butylaldehyde and the like. The aliphatic ketone is preferably an aliphatic ketone having 3 to 5 carbon atoms. Examples thereof include acetone, methyl ethyl ketone, diethyl ketone and the like. As described above, a zeolite containing titanium and silicon as zeolite constituent elements in which the atomic ratio of silicon to titanium is about 10 to about 500 and more preferably, about 20 to about 100 is used as the catalyst in the reaction of the present invention. Hereinafter, the above-described zeolite, which is used as the catalyst in the present invention, is referred to as titanium-silicate zeolite.

Another, feature of the present invention is that the as-prepared catalyst titanium-silicate is subjected to calcination at about 500-700° C. preferably in the presence of air or nitrogen or mixture thereof for about 6 to 24 hours to obtain organic free titanium-silicate zeolite which can optionally be subjected to 1 to 10 weight % aqueous solution of ammonium nitrate for ca. 1-4 hours at temperature at about 25 to 100° C., drying and calcining at about 500-700° C. in the presence of air or nitrogen or mixture thereof for about 6 to 24 hours.

Yet another feature of the present invention is that the zeolite titanium-silicate is loaded with other metal like lead, nickel, thallium or mixtures thereof using impregnation and or kneading method.

Yet another feature of the present invention is that the mixture of an aldehyde or ketone or mixture thereof as mentioned above and ammonia is contacted with catalyst titanium-silicate, prepared according to other features as mentioned above, in a gas phase at a temperature at about 300 to 500° C. at gas space velocity in the range of 300 to 3000 h$^{-1}$ at a reaction pressure at 1 atmospheric or more. After the reaction, the pyridine and/or picolines coming out of the reactor in a gaseous stream can be condensed and separated from the unconverted reactants, if any, recovered and purified using conventional methods like distillation or alternatively the reaction products substantially containing the pyridine and/or picolines are dissolved in a solvent and distilled to recover the pyridine and/or picolines.

Accordingly, the present invention provides an improved process for the preparation of pyridine and/or picolines which comprises contacting a mixture of carbonyl compound with ammonia in the presence of titanium-silicate catalyst in gas phase at a temperature ranging between 300-500° C., at gas space velocity in the range of 300 to 3000 h$^{-1}$ and at a pressure ranging between 1 to 10 atmosphere, condensing and separating the products by conventional methods, optionally further purifying the products using well known conventional methods.

In another embodiment, the titanium silicate catalyst is loaded with other metal like lead, nickel, thallium or mixtures thereof using impregnation/kneading method.

In one of the embodiments of the present invention, the carbonyl compound may be an aldehyde represented by formaldehyde, acetaldehyde, propionaldehyde or a ketone such as acetone, propionone and the like.

In another embodiment the catalyst used has molecular formula 1 SiO$_2$:x TiO$_2$, where x may be in the range of 0.005 and 0.05, having well crystalline structure characterized by powder X-ray diffraction pattern as described in Table 1.

In yet another embodiment of the present invention, the crystallite size of the catalyst used is in the range of 0.1-1.5 micron, more preferably, in the range of 0.3-0.6 micron.

In another embodiment of the present invention, the above crystallites of titanium silicate catalyst are treated with silicon tetrachloride or silicon tetraalkoxide using chemical vapour deposition method.

In yet another embodiment, the silicon tetraalkoxides may be selected from silicon-tetra-methoxide, silicon-tetra-ethoxide silicon-tetra-isopropoxide silicon-tetra-buoxide and the like.

TABLE 1

| 2 θ$^a$ | R.I.$^b$ |
|---|---|
| 7.86 | s |
| 8.78 | ms |
| 13.18 | w |
| 13.86 | mw |
| 14.74 | mw |
| 15.46 | mw |
| 15.89 | mw |
| 16.48 | mw |
| 17.26 | w |
| 17.64 | w |
| 17.82 | w |
| 19.22 | w |
| 20.36 | mw |
| 20.80 | mw |
| 22.20 | mw |
| 23.08 | vs |
| 23.90 | s |
| 24.40 | ms |
| 25.69 | mw |
| 25.85 | w |
| 26.64 | w |
| 27.42 | w |
| 29.26 | w |
| 29.90 | mw |

TABLE 1-continued

| 2 θ$^a$ | R.I.$^b$ |
|---|---|
| 45.10 | w |
| 45.52 | w |

$^a$the 2 θ values may vary by ±0.05
$^b$R.I. = Relative Intensity, vs = very strong, s = strong, m = medium, w = weak In yet another embodiment, the solid powder catalyst can optionally be mixed with inert binding substances like silica, alumina or mixture thereof and shaped in to extrudates or pallets as desired, dried and calcined or spray dried to obtain desired particle size, preferably, in the range of 50-100 microns.

The present invention will now be described in greater detail with reference to the following Examples, which are given by way of illustration and therefore, should not be construed to limit the scope of the present invention.

EXAMPLE 1

This example illustrates the preparation of titanium silicate molecular sieve with smaller crystallites. In a typical preparation 5 Kg of aqueous solution of tetra n-propyl ammonium hydroxide having 20% weight/weight (w/w) concentration was taken in a poly vinyl carbonate (PVC) container followed by the addition of 3.2 Kg of tetra ethyl ortho silicate(28% silica) under vigorous stirring to the above solution over a period of about 20 minutes. The mixture was stirred for 2 hours. A solution of 0.170 Kg of titanium butoxide in 0.700 Kg of isopropanol was added to the above mixture over a period of 10 min. This mixture was again stirred for 1 hour. Then 2.6 Kg of deionised water was added and the resulting mixture was vigorously mixed for 1 hour. The pH of the gel was measured to be about 12.5. The gel was then transferred to a 20 liter autoclave. The temperature was raised to 170° C. and this temperature was maintained for 24 hours and then the contents were cooled to room temperature. The resulting slurry was centrifuged and the solid product thus obtained was washed with deionised water. The wet cake was dried for 4 hours at 120° C. followed by calcination at 540° C. for 16 hours in presence of air. This sample so obtained is denoted as Catalyst-A. The particle size of the cuboid shaped crystallites of Catalyst-A was in the range of 0.1-0.3 micron.

EXAMPLE 2

This example also illustrates the synthesis of titanium silicate catalyst with medium range crystallite size. In atypical preparation, 5 Kg of aqueous solution of tetra n-propylammonium hydroxide 20% concentration w/w was taken in a PVC container followed by the addition 2.3 Kg. of ethyl silicate (40 wt. % Silica) was added slowly but with vigorous stirring to the above solution over a period of 20 min. The mixture was stirred for 2 hours. 0.170 Kg of titanium butoxide in 0.700 Kg isopropanol was added to the above mixture over a period of 10 minimum. This mixture was again stirred for 1 hour. Then 2.6 Kg of deionised water was added and the resulting mixture was vigorously mixed for 1 hour. pH of the gel was about 12.5 The gel was then transferred to a 20 l. autoclave. The temperature was raised to 170° C. This temperature was maintained for 24 hours and then the contents are cooled. The resulting slurry was centrifuged and the solids are washed with deionised water.

The wet cake was dried for 4 hours at 120° C. It was then calcined at 540° C. for 16 hrs. in presence of air. This sample so obtained was denoted as Catalyst-B. The particle size of the cuboid shaped crystallites of Catalyst-B was in the range of 0.4-0.6 micron.

EXAMPLE 3

This example illustrates the preparation of titanium silicate catalyst sample C. In a typical preparation, 5 Kg aqueous solution of tetra-n-propyl-ammonium hydroxide (20% w/w) was taken in a PVC container followed by the addition 2.3 Kg. of ethyl silicate (40% Silica) which was added slowly but with vigorous stirring to the above solution over a period of 20 min. The mixture was stirred for 2 hours. 0.170 Kg of titanium butoxide in 0.700 Kg. isopropanol was added to the above mixture over a period of 10 min. This mixture was again stirred for 1 hour. Then 2.6 Kg of deionised water was added and the resulting mixture was vigorously mixed for 1 hour. The gel was then transferred to a 20 l. autoclave. The temperature was raised in stepwise manner in first step the temperature of the reaction mixture was raised up to 100° C. and was maintained for 12 h and then further raised to finally 170° C. This temperature was maintained for 24 hours and then the contents are cooled. The resulting slurry was centrifuged and the solids are washed with deionised water. The wet cake was dried for 4 hours at 120° C. It was then calcined at 540° C. for 16 hrs. in presence of air. The particle size of cuboid shaped crystallites of the catalyst, denoted as Catalyst-C, was in the range of 0.3-0.6 micron.

EXAMPLE 4

This example illustrates the preparation of titanium-silicate catalyst sample D. 2.5 Kg of aqueous solution of tetra-n-propyl-ammonium hydroxide 20% concentration w/w was taken in a PVC container followed by the addition 2.3 Kg. of ethyl silicate (40% Silica) which was added slowly but with vigorous stirring to the above solution over a period of 20 min. The mixture was stirred for 2 hours. 0.170 Kg of titanium butoxide in 0.700 Kg. isopropanol was added to the above mixture over a period of 10 min. This mixture was again stirred for 1 hour. Then 2.6 Kg of deionised water was added and the resulting mixture was vigorously mixed for 1 hour. pH of the gel was about 12.5 The gel was then transferred to a 20 l. autoclave. The temperature was raised to 170° C. This temperature was maintained for 24 hours and then the contents are cooled. The resulting slurry was centrifuged and the solids are washed with deionised water. The wet cake was dried for 4 hours at 120° C. It was then calcined at 540° C. for 16 hrs. in presence of air. This sample was denoted as Catalyst-D. The particle size of the cuboid shaped crystallites of catalyst -D sample was in the range of 1.0 to 1.5 micrometer.

EXAMPLE 5

This example illustrates the preparation of amorphous titanium-silicate for comparative study. 5 Kg of aqueous solution of Tetra n-propyl ammonium hydroxide 20% concentration w/w was taken in a PVC container followed by the addition of ethylsilicate slowly but with vigorous stirring to the above solution over a period of 20 min. The mixture was stirred for 2 hours. 0.170 Kg of Titanium Butoxide in 0.700 Kg. isopropanol was added to the above mixture over a period of 10 min. This mixture was then evaporated to dryness at room temperature and the solid thus obtained was then calcined at 540° C. for 16 hours in the presence of air. This amorphous titanium-silicate sample so obtained is denoted as Catalyst-E.

EXAMPLE 6

This example illustrates the surface passivation of the external surface of the crystallites of catalysts A and B. A gaseous mixture containing nitrogen and the vapors of tetra ethyl orthosilicate, where the nitrogen was contacted with tetraethylorthoisilicate filled in a saturator at 15° C. This gaseous mixture was then contacted with 100 g of the Catalyst-A at temperature 120° C. for 8 hours followed by the flushing of the catalyst with dry nitrogen (10 l per minute) for 30 minutes and the catalyst was subjected to calcinations in the presence of an air flow (10 l per hour) at 500° C., where the temperature was raised from 100° C. to 500° C. with a heating rate of 5° C. per minute, for 4 hours. This procedure was repeated twice and the resultant catalysts is denoted as Catalyst A-passivated.

The same procedure, as mentioned above was used to treat the catalyst B for passivation, where Catalyst B was used in place of Catalyst-A, and the sample thus obtained was denoted as catalyst B-passivated.

EXAMPLE 7

This example illustrates the loading of metal such as lead on calcined titanium-silicate catalyst using impregnation/kneading method. In a typical method, 250 gm of catalyst was contacted under stirring condition with a solution containing 31 g lead nitrate in 350 gm of water. The whole slurry was then evaporated to dryness and the solid thus obtained was dried at 120° C. for 5 hours, followed by calcination at 550° C. in the presence of air for 5 hours. It is preferred that final Titanium-Silicate should contain Pb in an amount of 4-7% by weight in terms of metal. Similarly, other metals can also be loaded in the range of 3.5-12% w/w.

EXAMPLE 9

This example illustrates the method for carrying out catalytic reaction. Catalyst samples A to E, prepared by kneading method with 4.5 wt. % loading of lead and containing 17 wt. % binder were pelletized and evaluated in SS 316 reactor tube with 31 mm I.D and 750 cc catalyst capacity, down flow, fixed bed reactor. A mixed gas of acetaldehyde and ammonia optionally along with water/steam as diluent were pre-heated at 250-300° C. and the vapours allowed to pass over the catalyst bed kept at isothermal condition. Catalyst bed temperature was maintained between 390-400° C. The exit gases containing the pyridine bases were condensed and analyzed for the components. Finally, the resultant condensate or the reaction mass is extracted with a solvent and fractionated to recover the pyridine bases. After prolonged reaction when the catalyst gets de-activated, it is regenerated by passing air at 500-550° C. Preferably, air is diluted with nitrogen during the regeneration of the catalyst. The results obtained with different catalysts are given in Table-2. It is clear from the data given in Table-2 that the catalyst B with crystallite size of 0.4-0.6 micron and C with crystallite size of 0.4 and 0.6 are significantly more productive compared to catalyst A, with crystallite size of 0.1-0.3, catalyst D with crystallite size of 1.0-1.5 as well as amorphous catalyst E. To study the effect of surface passivation, the above mentioned procedure for carrying out catalytic reaction was employed, where the catalysts used were Catalyst A-passivated and Catalysts B-passivated and the results are tabutaled in Table 3.

TABLE 2

Comparison of catalytic performance of different catalysts.

| Parameters | Cat. A | Cat. A | Cat. B | Cat. C | Cat. D | Cat. E |
|---|---|---|---|---|---|---|
| Crystallite size μm | 0.1-0.3 | 0.1-0.3 | 0.4-0.6 | 0.6-0.8 | 1.0-1.5 | N.A. |
| Space velocity/h | 512 | 633 | 884 | 894 | 588 | 526 |
| Conversion, % | 96.5 | 93.0 | 94.3 | 94.7 | 96.5 | 88.0 |
| Pyridine, % | 0.91 | 0.90 | 1.11 | 0.88 | 0.92 | 0.78 |
| Alpha picoline % | 51.66 | 45.9 | 51.32 | 53.44 | 50.3 | 17.3 |
| Gamma picoline % | 20.35 | 17.1 | 21.71 | 20.55 | 18.95 | 9.54 |
| Total % | 72.92 | 63.9 | 74.14 | 74.87 | 70.17 | 27.62 |
| Selectivity, % | 74.6 | 67.7 | 77.4 | 78.10 | 71.80 | 30.5 |
| Picolines Yield, % | 72.01 | 63.0 | 73.03 | 73.99 | 69.25 | 26.84 |
| Alpha:Gamma ratio | 2.54 | 2.6 | 2.36 | 2.60 | 2.6 | 1.8 |

TABLE 3

Comparison of catalyst with and without surface passivation

| Parameters | Catalyst-A | Catalyst-A-passivated | Catalyst-B | Catalyst-B-passivated |
|---|---|---|---|---|
| Space velocity/h | 512 | 512 | 884 | 884 |
| Conversion, % | 96.5 | 96.0 | 94.3 | 94.0 |
| Picoline Selectivity, % | 74.6 | 83.4 | 77.4 | 85.7 |
| Picolines Yield, % | 72.01 | 80.0 | 73.03 | 80.5 |
| Alpha:Gamma ratio | 2.54 | 2.4 | 2.4 | 2.6 |

We Claim:

1. In a process for the preparation of a picoline, which comprises a) contacting a mixture of a carbonyl compound, which is an aldehyde or ketone, with ammonia in the presence of a titanium-silicate catalyst in gas phase at a temperature ranging between 300-500° C., at a gas space velocity ranging between 300 to 3000h$^{-1}$ and at a pressure ranging between 1 to 10 atmospheres to obtain resultant products comprising the picoline, and (b) recovering the picoline in purified form, wherein the improvement comprises the titanium-silicate catalyst has an external surface that has been selectively passivated.

2. The process as in claim 1, wherein the carbonyl compound is an aldehyde selected from the group consisting of formaldehyde, acetaldehyde and propionaldehyde.

3. The process as claimed in claim 1, wherein the carbonyl compound is formaldehyde.

4. The process as claimed in claim 1, wherein the catalyst has a molecular formula of 1 SiO$_2$:x TiO$_2$, where x is in a range of 0.005 to 0.05, and wherein the catalyst has a crystalline structure characterized by a powder X-ray diffraction pattern as shown in Table 1.

5. The process as claimed in claim 1, wherein the catalyst comprises crystallites with a crystallite size in a range of 0.1 to 1.5 microns.

6. The process as claimed in claim 1, wherein the catalyst comprises crystallites with a crystallite size in a range of 0.3 to 0.8 microns.

7. The process as claimed in claim 1, wherein the external surface of the catalyst has been selectively passivated by treatment of the catalyst with silicon tetrachloride or silicon tetraalkoxide by chemical vapor deposition.

8. The process as claimed in claim 7, wherein the treatment is with a silicon tetraalkoxide selected from the group consisting of silicon-tetra-methoxide, silicon-tetra-ethoxide, silicon-tetra-isopropoxide and silicon-tetra-butoxide.

9. The process as claimed in claim 5, wherein the external surface of the catalyst has been selectively passivated by treatment of the catalyst with silicon tetrachloride or silicon tetraalkoxide by chemical vapor deposition.

10. The process as claimed in claim 9, wherein the treatment is with a silicon tetraalkoxide selected from the group consisting of silicon-tetra-methoxide, silicon-tetra-ethoxide, silicon-tetra-isopropoxide and silicon-tetra-butoxide.

11. The process as claimed in claim 1, further comprising, after step a), loading the catalyst with a metal.

12. The process as claimed in claim 11, wherein the metal is selected from the group consisting of lead, nickel, thallium and mixtures thereof.

13. The process as claimed in claim 1, wherein the catalyst is prepared as a solid powder which is optionally mixed with an inert binding substance, shaped into an extrudate or pellet, and then dried and calcined or spray dried to obtain a desired particle size.

14. The process as claimed in claim 13, wherein the desired particle size is in a range of 50 to 100 microns.

15. The process as claimed in claim 1, wherein the catalyst is prepared by selectively passivating the external surface of a titanium-silicate catalyst A, B, C, D or E shown in Table 2.

16. The process as claimed in claim 15, wherein the resultant products comprise a mixture of pyridine and the picoline, said titanium-silicate catalyst with the external surface that has been selectively passivated providing the process with an increased yield and selectivity for the picoline as compared with the catalyst before the passivation.

17. The process as claimed in claim 1, wherein the external surface of the catalyst has been selectively passivated by selective in-situ deposition of silica onto the external surface.

18. In a process for the preparation of picoline, which comprises a) contacting a mixture of a carbonyl compound, which is an aldehyde or ketone, with ammonia in the presence of a titanium-silicate catalyst in gas phase at a temperature ranging between 300-500° C., at a gas space velocity ranging between 300 to 3000h$^{-1}$ and at a pressure ranging between 1 to 10 atmospheres to obtain resultant products comprising a mixture of the picoline and a pyridine, and (b) recovering the picoline in purified form, wherein the improvement comprises the titanium-silicate catalyst has an external surface that has been selectively passivated such that a yield and selectivity for the picoline is higher than with the catalyst before the passivation.

19. The process as claimed in claim 18, wherein the external surface of the catalyst has been selectively passivated by treatment of the catalyst with silicon tetrachloride or silicon tetraalkoxide by chemical vapor deposition.

20. The process as claimed in claim 18, wherein the external surface of the catalyst has been selectively passivated by selective in-situ deposition of silica onto the external surface.

* * * * *

UNITED STATES PATENT AND TRADEMARK OFFICE
CERTIFICATE OF CORRECTION

| | |
|---|---|
| PATENT NO. | : 7,365,204 B2 |
| APPLICATION NO. | : 10/806061 |
| DATED | : April 29, 2008 |
| INVENTOR(S) | : Rajiv Kumar et al. |

It is certified that error appears in the above-identified patent and that said Letters Patent is hereby corrected as shown below:

On title page, item 73, "Jubliant" should read -- Jubilant --.

Signed and Sealed this

Ninth Day of December, 2008

JON W. DUDAS
*Director of the United States Patent and Trademark Office*